United States Patent
Wells et al.

(10) Patent No.: US 12,138,099 B2
(45) Date of Patent: Nov. 12, 2024

(54) X-RAY DIGITAL TOMOSYNTHESIS SYSTEM AND METHOD

(71) Applicant: ADAPTIX LTD, Begbroke (GB)

(72) Inventors: Steve Wells, Begbroke (GB); Kristin Schmiedehausen, Begbroke (GB)

(73) Assignee: ADAPTIX LTD, Begbroke (GB)

( * ) Notice: Subject to any disclaimer, the term of this patent is extended or adjusted under 35 U.S.C. 154(b) by 288 days.

(21) Appl. No.: 17/692,826

(22) Filed: Mar. 11, 2022

(65) Prior Publication Data

US 2022/0192618 A1 Jun. 23, 2022

Related U.S. Application Data

(63) Continuation of application No. PCT/GB2020/052185, filed on Sep. 10, 2020.

(30) Foreign Application Priority Data

Sep. 12, 2019 (GB) .................................... 1913166

(51) Int. Cl.
*A61B 6/00* (2024.01)
*A61B 6/02* (2006.01)

(52) U.S. Cl.
CPC ................ *A61B 6/54* (2013.01); *A61B 6/025* (2013.01); *A61B 6/5205* (2013.01)

(58) Field of Classification Search
CPC .... A61B 6/00; A61B 6/02; A61B 6/54; A61B 6/025; A61B 6/5205; A61B 6/035; A61B 6/4007; A61B 6/4085; A61B 6/4429; A61B 6/488; A61B 6/5241; A61B 6/58
See application file for complete search history.

(56) References Cited

U.S. PATENT DOCUMENTS

2018/0289348 A1   10/2018   Cox et al.

FOREIGN PATENT DOCUMENTS

| EP | 2554119 | 2/2013 |
|----|---------|--------|
| EP | 3407793 | 3/2020 |
| JP | 2009115462 | 5/2009 |

(Continued)

OTHER PUBLICATIONS

UKIPO, Search Report in corresponding GB application GB1913166.3, Feb. 3, 2020.

(Continued)

*Primary Examiner* — Jurie Yun
(74) *Attorney, Agent, or Firm* — Alley IP (57) ABSTRACT

Alignment of tomosynthesis systems requires operator skill, particularly where regions of interest are internal structures with limited surface features. Reconstruction of an entire 3D tomosynthesis image may require seconds to minutes, and it can take this long before operators realize that subsequent scans are required. In this time, the patient may have moved and a second scan could also potentially miss the region of interest, requiring a third scan, etc. Multiple exposures are time-consuming and increase patient radiation dose. A digital x-ray tomosynthesis system comprises a static array of x-ray emitters and an x-ray detector and involves selecting a sub-set of x-ray emitters so no x-ray detector part is exposed to x-rays from more than nine of the sub-set and generating a composite image from non-overlapping portions of each respective image produced on the x-ray detector. A two-dimensional image of a subject may be produced using minimal radiation dose.

10 Claims, 7 Drawing Sheets

(56) References Cited

FOREIGN PATENT DOCUMENTS

| | | |
|---|---|---|
| JP | 2019-506207 | 3/2019 |
| WO | 2009012453 | 1/2009 |
| WO | 2017130018 | 8/2017 |
| WO | 2019102216 | 5/2019 |

OTHER PUBLICATIONS

WIPO, International Search Report and Written Opinion in corresponding PCT application PCT/GB2020/052185, Jan. 25, 2021.
UKIPO, Search Report in corresponding GB application GB1913166.3, Nov. 1, 2022.
UKIPO, Search Report in corresponding GB application GB1913166.3, Jul. 25, 2022.
JPO, Notice of Refusal in corresponding JP Application 2022-516053, Apr. 9, 2024.

FIG. 7

X-RAY DIGITAL TOMOSYNTHESIS SYSTEM AND METHOD

RELATED APPLICATIONS

This application claims the benefit under 35 U.S.C. § 120, and is a continuation, of co-pending International Application PCT/GB2020/052185, filed Sep. 10, 2020 and designating the US, which claims priority to GB Application 1913166.3, filed Sep. 12, 2019, such GB Application also being claimed priority to under 35 U.S.C. § 119. These GB and International applications are incorporated by reference herein in their entireties.

FIELD

The present invention relates generally to digital tomosynthesis and a method of recovering a 2D image and finds particular, although not exclusive, utility in x-ray digital tomosynthesis.

BACKGROUND 3D medical imaging using x-rays has been possible since the invention of computed tomography (CT) imaging in the 1970s. In recent years, x-ray digital tomosynthesis (DT) techniques have been developed which offer the possibility of 3D image reconstruction at lower cost and dose, by using static arrays of x-ray sources to perform tomosynthesis acquisitions.

SUMMARY

Initial alignment of a tomosynthesis system, in order to correctly image a region of interest, requires skill on the part of the operator, particularly where the region of interest is an internal structure with only limited surface features. Occasionally, even the most skilled operators incorrectly align an emitter array and detector, which results in an unnecessary dose of radiation to the subject (be it a person, animal, sample or device).

In addition, it can be tens of seconds, sometimes minutes, to reconstruct an entire 3D tomosynthesis image, and therefore it can take this long before an operator realizes that the positioning was sub-optimal and that a subsequent scan is required. In this time, the patient may have moved and a second scan could also potentially miss the region of interest, requiring a third scan, and so on.

Multiple exposures are not only time-consuming, but also increase the dosage of radiation received by a patient.

It is therefore apparent that there is a need to provide a low-dose 'scout' image to assist operators in positioning their patients, emitters and detectors, and also to reduce the risk of higher x-radiation doses being received by patients.

According to a first aspect of the present invention, there is provided a digital x-ray tomosynthesis system comprising: an x-ray emitter panel comprising a plurality of spatially distributed x-ray emitters arranged in a substantially planar array such that each respective emission cone from each respective one of the plurality of x-ray emitters projects along a respective axis substantially perpendicular to the planar array, when activated; an x-ray detector spaceable from the x-ray emitter panel by a separation distance such that each respective emission cone from each respective one of the plurality of x-ray emitters impinges on the x-ray detector, when activated; a controller configured to: select a sub-set of x-ray emitters from the plurality of x-ray emitters such that: no part of the x-ray detector, or corresponding region of interest, is exposed to x-rays from more than nine x-ray emitters of the sub-set of x-ray emitters; activate each x-ray emitter of the sub-set of x-ray emitters in a sequence to produce a respective image at the x-ray detector; and generate a composite image from non-overlapping portions of each of the respective images produced on the x-ray detector; and an output device configured to display the composite image generated by the controller.

In this way, a representative but incomplete two-dimensional image of a subject may be produced using a minimal dosage of radiation.

The x-ray emitter panel may comprise a substantially flat surface. Alternatively or additionally, the panel may comprise a curved surface, e.g. convex or concave, with a radius of curvature of at least 50 cm, in particular at least 1 m, more particularly at least 2 m.

The plurality of spatially distributed x-ray emitters may comprise individual emitters arranged in a triangular array, square array, rectangular array, hexagonal array and/or any other configuration. The plurality of emitters may comprise a 5×5 array, a 10×10 array, a 20×20 array or a 30×30 array. The plurality of emitters may comprise at least 25 emitters, in particular at least 100 emitters, more particularly at least 200 emitters, for example at least 400 emitters.

The emission cone may comprise a conelet, and may have a shape of a geometric cone and/or a square or triangular base pyramid. The cone may project along the respective axis in that the cone may be rotationally symmetric about the respective axis; e.g., having two-fold, three-fold, four-fold, five-fold, six-fold or circular symmetry.

Substantially perpendicular to the planar array may comprise being at most 20 degrees from the normal at that part of the planar array, in particular at most 10 degrees, more particularly at most 5 degrees. Moreover, each respective axis may be substantially parallel to each other axis, for example differing in inclination by at most 20 degrees, in particular by at most 10 degrees, more particularly at most 5 degrees.

Activation of an emitter involves emitting x-rays from that emitter. When x-rays are not being emitted, the emitter is inactive.

The x-ray detector may comprise an array of pixels. The detector may form part of a larger detector panel (e.g., comprising additional pixels), or may comprise an entire detector panel. The detector may have a lateral extent of between 10 cm and 60 cm, in particular between 20 cm and 50 cm, more particularly approximately 40 cm. For example, the detector may measure approximately 36 cm×43 cm.

The x-ray emitter panel may be spaced from the detector during operational use (i.e., activation) by a separation distance. The distance may be between 10 cm and 1 m, in particular between 20 cm and 80 cm, more particularly between 30 cm and 70 cm, for example approximately 50 cm.

A spatial tracker may monitor this distance for use by the controller. The spatial tracker may be an automated system, based on determining location of registry pins, etc., and/or the spatial tracker may be manually implemented (e.g., an operator may measure/estimate the distance and input that distance determination into the controller).

The emitter panel may comprise a further plurality of spatially distributed x-ray emitters. For example, each respective emission cone from each respective one of the further plurality of x-ray emitters may not impinge on (i.e. miss) the x-ray detector, if activated. Alternatively, the first plurality of spatially distributed x-ray emitters may compose all of the emitters on the emitter panel.

Impinging on the x-ray detector may comprise wholly and/or at least or only partially impinging on the detector.

The controller may comprise a computer system, processor, etc.

The term 'select' may mean 'choose'; this may be automatic, and/or may involve operator input.

The sub-set may mean only one or a plurality; for example, three, at least three, four, at least four, or at least six, nine, twelve, sixteen, twenty or twenty-five.

No part of the x-ray detector may be exposed to x-rays from more than eight, seven, six, five, four, three, two or one x-ray emitter(s) of the sub-set of x-ray emitters.

The controller may be configured to select the sub-set of x-ray emitters from the plurality of x-ray emitters such that each part of the x-ray detector, or corresponding region of interest, is exposed to x-rays from at least one x-ray emitter of the sub-set of x-ray emitters, when activated.

In this way, full coverage of the subject may be obtained for creation of a 2D image.

The controller may be configured to select the sub-set of x-ray emitters from the plurality of x-ray emitters such that at least one part of the x-ray detector is not exposed to x-rays from any x-ray emitter of the sub-set of x-ray emitters, when activated.

In this way, unnecessary exposures can be eliminated where full coverage of the subject is not required. For example, the 2D image produced may be an outline of the subject, or merely the corners of the region of interest, to help with alignment of the system/emitters/detector.

The respective cones of x-rays may project a predetermined/predefined pattern of shapes, e.g. circles, ellipses, or potentially squares, rectangles or triangles for pyramid shape conelets. The shapes may partially overlap adjacent shapes, or may be spaced from adjacent shapes.

A degree of overlap may be inferred from the spacing of the emitter panel from the detector, or the degree of overlap may be calculated from the size and shape of a first emitter's projected shape on the detector. That is, a first emitter may be activated, and subsequent emitters may be activated in response to detecting the size, shape and/or location of the image formed at the detector. This process may be repeated with a second, third or further emitter.

The system may be configured to determine overlap of each of the respective images by analyzing the subject-matter of the images. That is, each image may be analyzed to determine how much the emission cones of each respective one of the plurality of x-ray emitters overlaps within a region of interest. For example, a subject may be placed between the emitter panel and detector such that it is spaced from the detector. Overlap at the detector may therefore not correspond to overlap within the subject. As a further alternative/addition, a spacing of a region of interest from the detector may be established (such as by operator input or by inference from analysed images) and that spacing may be used to calculate an overlap.

Overlap of any two emission cones on the detector or the region of interest may be by less than 30% area, in particular less than 20% area, more particularly less than 10% area, for example, 5% area.

The controller is configured to select the sub-set of x-ray emitters from the plurality of x-ray emitters before activation of all x-ray emitter of the sub-set of x-ray emitters to produce the respective images at the x-ray detector.

In this way, a 2D scout image may be provided such that the sub-set of emitters is activated first to generate/calculate the composite image, and then that image is presented to an operator to allow them to determine whether the emitter panel and detector is correctly positioned before the remainder of the emitters are activated.

All the sub-set of x-ray emitters may be selected before any of the sub-set of x-ray emitters are activated. Alternatively, the selection may be dynamic in that a first emitter may be selected and activated, and in response to the image produced a second emitter may be selected and activated, etc. until all emitters in the sub-set have been selected and activated. However, other schemes in which groups of emitters are selected and activated before others are selected are envisaged.

These selection steps may be automatic, or may be operator-led.

The controller may be configured to activate each x-ray emitter of the plurality of x-ray emitters to produce a respective image at the x-ray detector and to reconstruct a 3D tomosynthesis image from the images at the x-ray detector produced by the plurality of x-ray emitters, in response to an input indicating acceptance of the composite image.

In this way, operator feedback may be required to confirm an acceptable position of a subject, the emitter panel and/or detector before full tomosynthesis acquisition. Alternatively, the input may be performed automatically by a feature detection component; e.g. to identify lung, breast and/or skeletal tissue.

The controller may be configured to activate each x-ray emitter of the plurality of x-ray emitters to produce a respective image at the x-ray detector, and subsequently generate the composite image from non-overlapping portions of each of the respective images produced by the sub-set of the x-ray emitters.

In this way, a 2D preview image may be presented to the operator for review prior to presenting any 3D reconstruction that may be performed.

It is to be understood that a 2D scout image and a 2D preview image are not simple alternatives, but could both be performed once or more than once during a single imaging sequence. For example, a first 2D scout image could be taken and reviewed and the emitter panel and/or detector could be moved in response thereto, then a second 2D scout image could be taken and accepted/approved; a full tomosynthesis acquisition (i.e., with all relevant emitters) could then be taken and a 2D preview provided to the operator prior to full tomosynthesis reconstruction being completed.

The controller may be configured to reconstruct a 3D tomosynthesis image from the images at the x-ray detector produced by the plurality of x-ray emitters.

The controller may be configured to reconstruct the 3D tomosynthesis image at the same time as generating the 2D preview image from the non-overlapping portions of each of the respective images produced by the sub-set of the x-ray emitters.

In this way, the preview could be presented to the operator before completion of the full tomosynthesis reconstruction, but not hindering the full tomosynthesis reconstruction.

The controller may be configured to reconstruct the 3D tomosynthesis image after generating the 2D preview image from the non-overlapping portions of each of the respective images produced by the sub-set of the x-ray emitters.

In this way, the 2D preview may be presented to the operator as quickly as possible, without waiting for a full tomosynthesis reconstruction to complete. For example, full tomosynthesis reconstruction may be performed immediately after the 2D preview is formed.

The emitters may be activated spaced from one another in time or space; i.e., emitters with overlapping cones of x-rays may be activated at different times, whereas emitters with non-overlapping cones of x-rays may be activated at same time or at different times.

The composite image may be formed by combining the plurality of respective images together.

The composite image may be formed using non-overlapping portions of each respective image from each x-ray emitter of the sub-set of x-ray emitters. That is, each respective image may be cropped so as not to overlap with an adjacent image.

The composite image may be formed from such respective images to form a continuous composite image, or the composite image may be formed from such respective images spaced from one another. The region between such spaced respective images may be white, black or a neutral color such as grey; in particular, the color may be an average of the intensities from the respective images.

The output device may comprise a display connected to the controller. The output device may be configured to display the composite image to an operator as soon as practical after it is generated.

According to a second aspect of the present invention, there is provided a method of presenting a 2D composite image to a user, the method comprising the steps of: providing the system of any preceding claim; selecting a sub-set of x-ray emitters from the plurality of x-ray emitters such that no part of the x-ray detector, or corresponding region of interest, is exposed to x-rays from more than nine x-ray emitters of the sub-set of x-ray emitters; activating each x-ray emitter of the sub-set of x-ray emitters to produce a respective image at the x-ray detector; and generating a composite image from non-overlapping portions of each of the respective images produced on the x-ray detector.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

Figure 1:
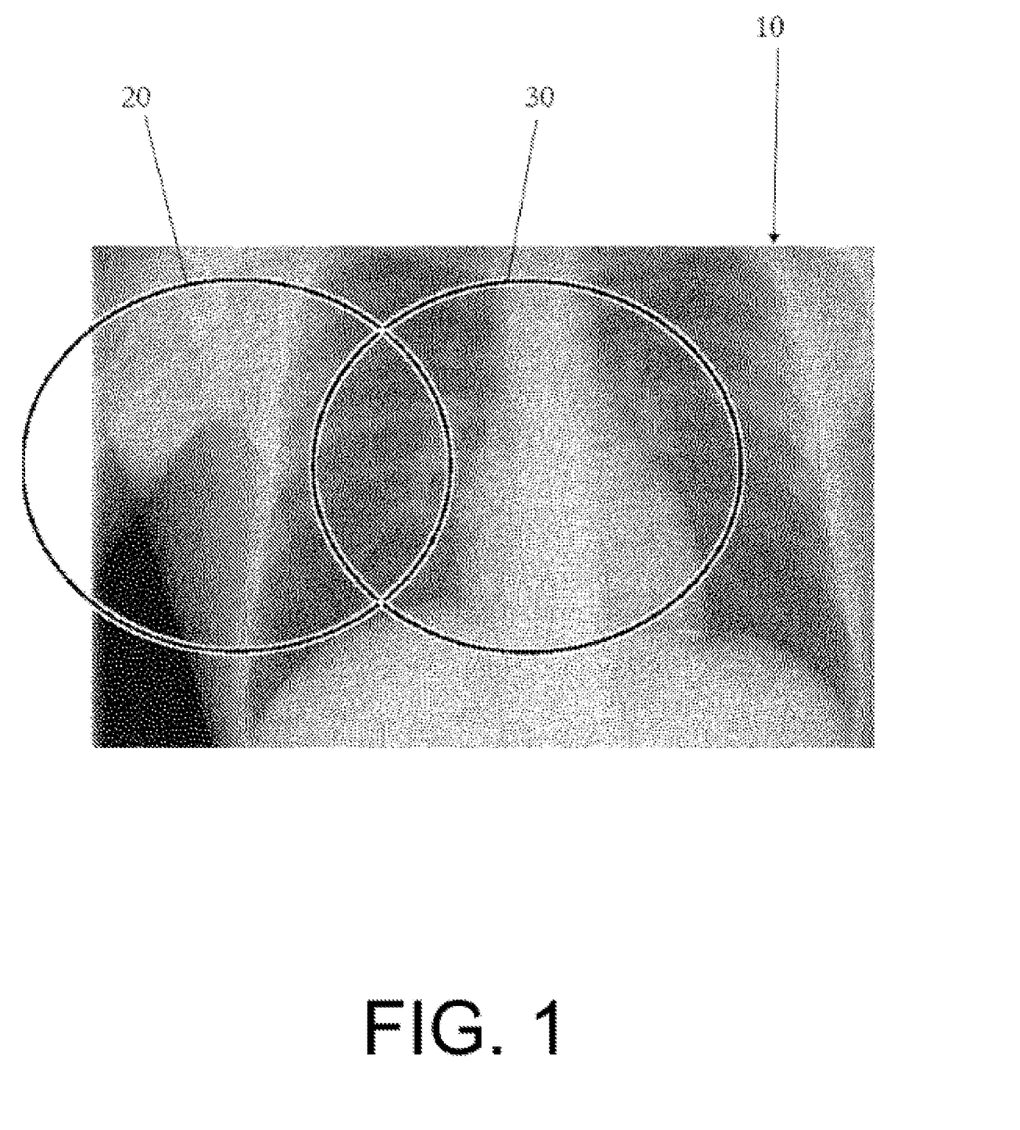
FIG. 1 is a view of two overlapping cones of x-rays projected onto a detector to form two overlapping ellipse regions.

FIG. 1 shows a conventional 2D x-ray of a subject's torso 10, with overlaid a first elliptical region 20 formed from projecting a single conelet of x-rays from a first emitter onto a detector, and a second elliptical region 30 formed in a similar manner from a second emitter, partially overlapping the first elliptical region 20.

Figure 2:
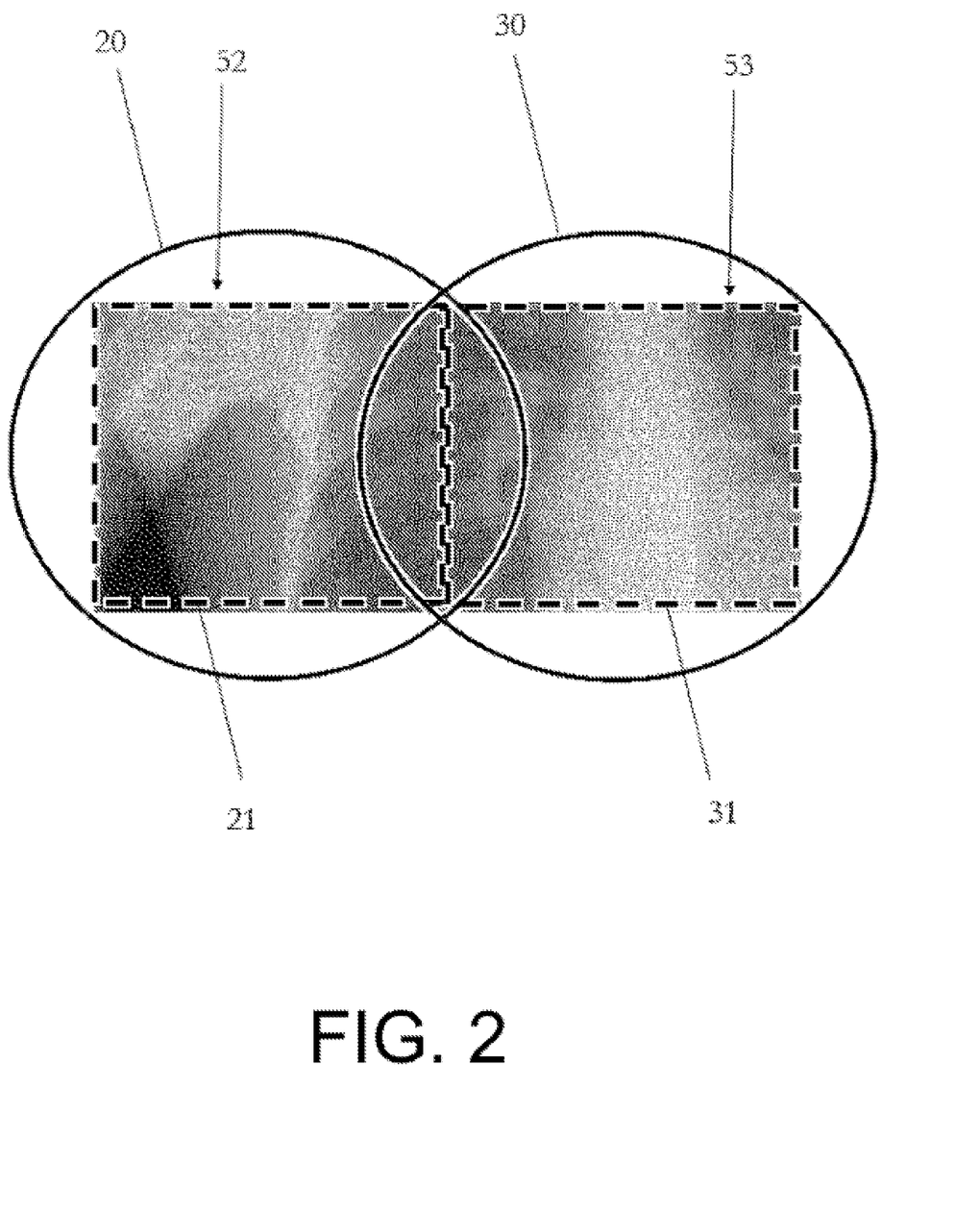
FIG. 2 is a view of the two overlapping ellipse regions of FIG. 1, having been cropped to two non-overlapping rectangular regions.

FIG. 2 shows the respective images 52, 53 formed at the detector by the conelets referred to in FIG. 1, the first elliptical region 20 and the second elliptical region 30 each having been cropped to non-overlapping rectangular regions 21, 31.

Figure 3:
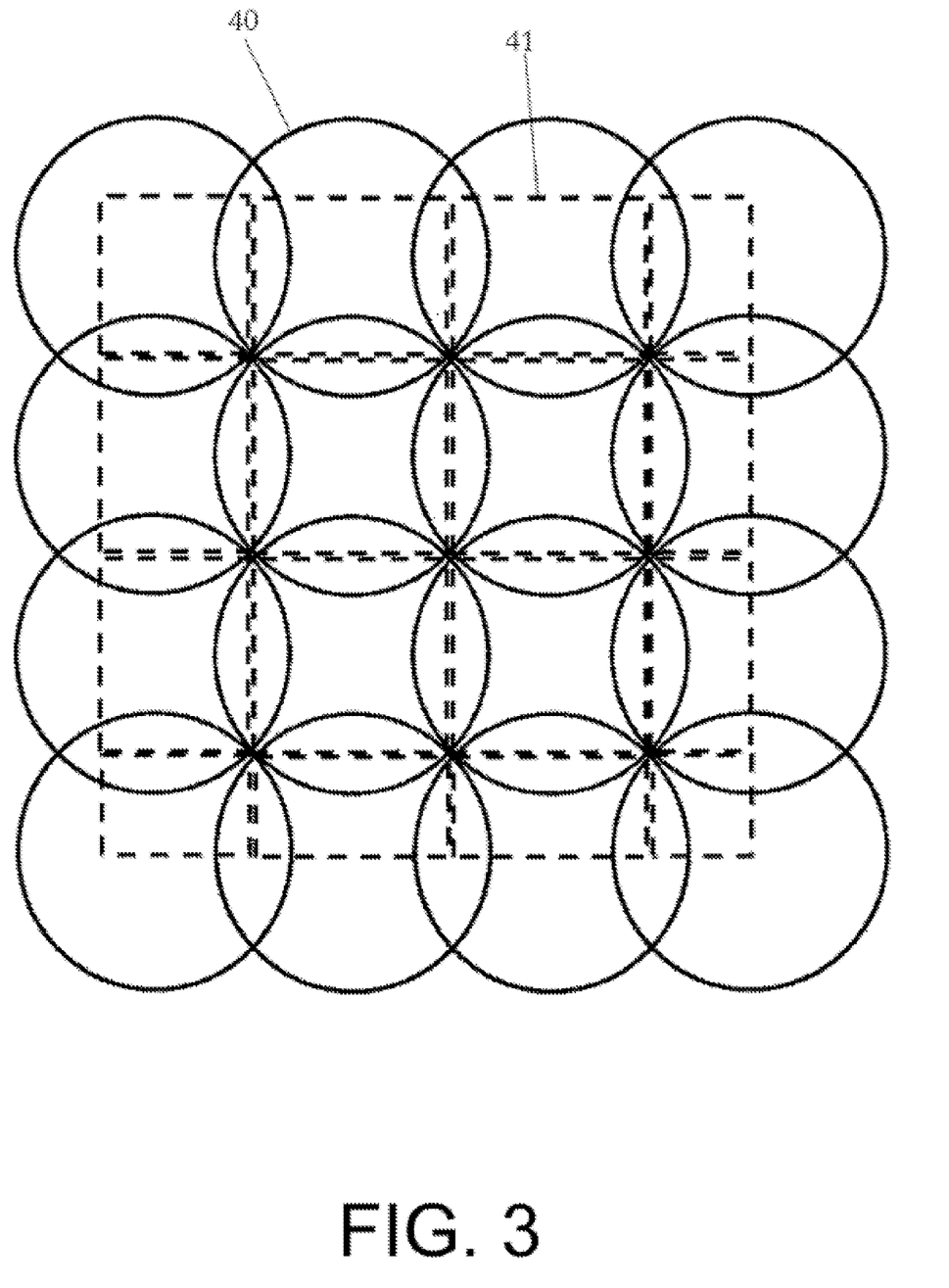
FIG. 3 shows sixteen overlapping ellipse regions, similar to those of FIGS. 1 and 2, and the corresponding cropped non-overlapping rectangular regions.

FIG. 3 shows sixteen overlapping ellipse regions 40, similar to those of FIGS. 1 and 2, and the corresponding cropped non-overlapping rectangular regions 41 formed on the display.

Figure 4:
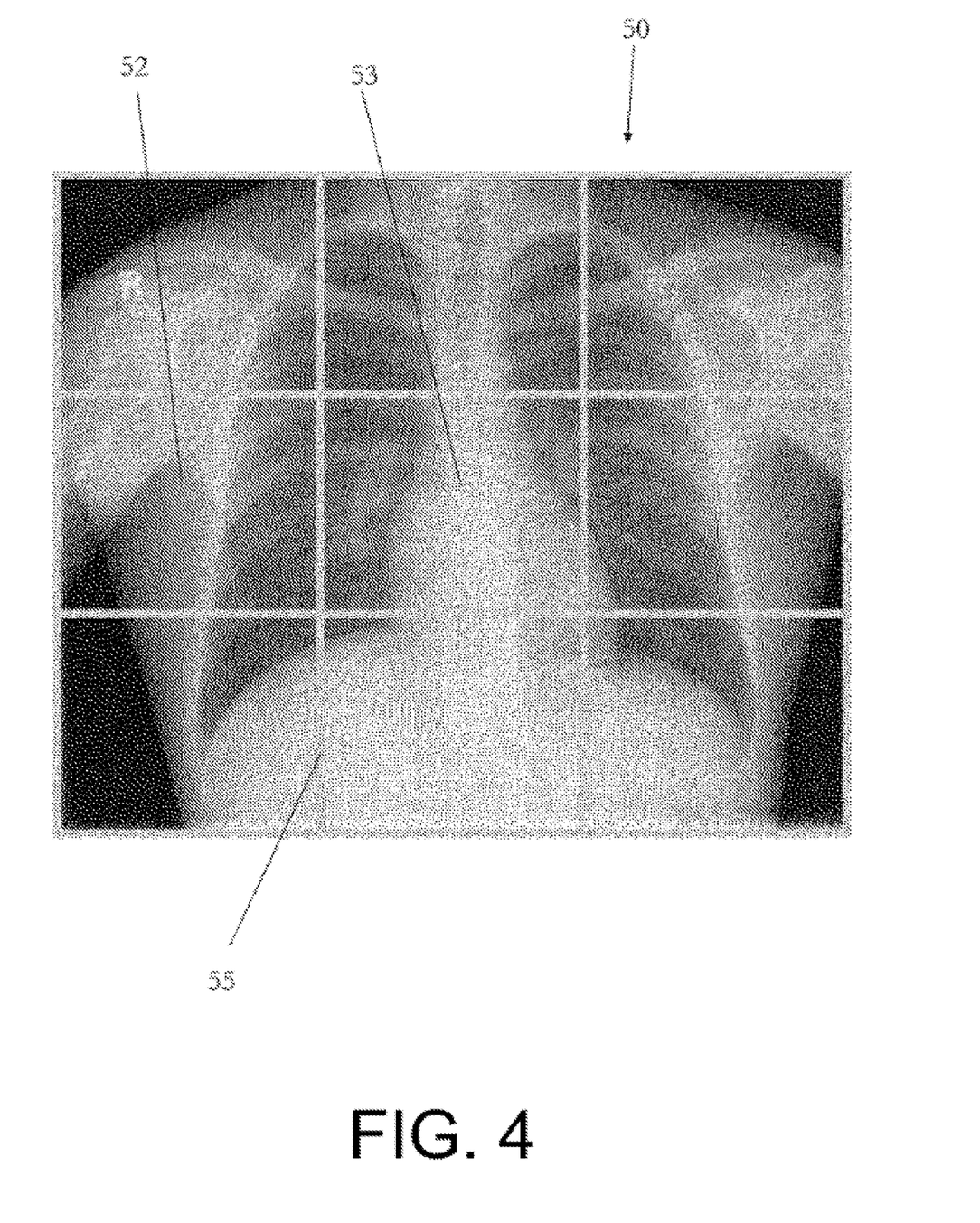
FIG. 4 shows a composite image formed from nine adjacent non-overlapping rectangular regions similar to those of FIG. 2.

FIG. 4 shows a composite image 50, corresponding to the conventional 2D x-ray of a subject's torso 10 of FIG. 1, formed from nine adjacent non-overlapping rectangular regions, including the respective images 52, 53 of FIG. 2, with the rectangular regions and the ellipses from which they are formed omitted for clarity. As can be seen, the non-overlapping respective images are non-contiguous, and are spaced apart from one another using a grid 55 having a color that is the average intensity from the respective images.

Figure 5:
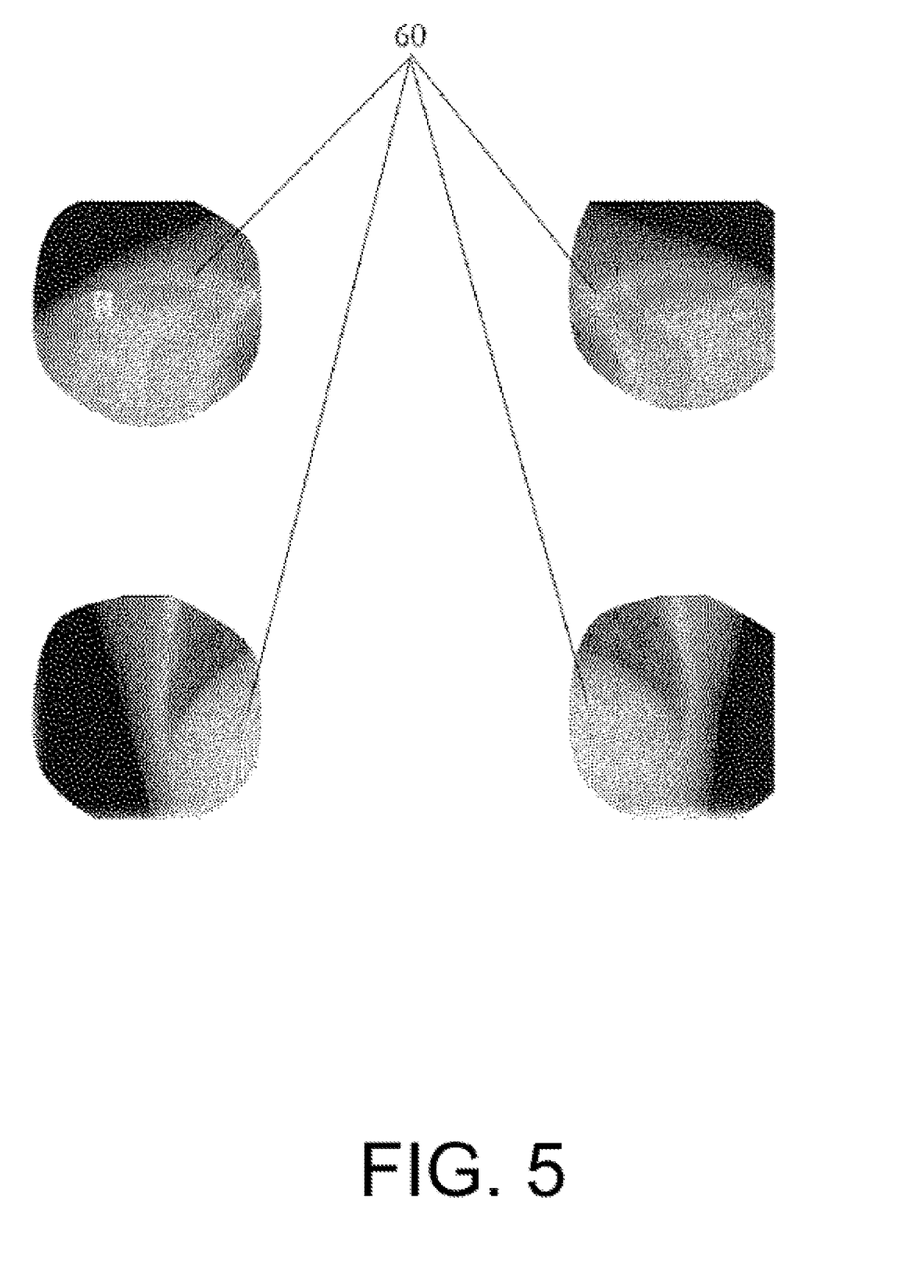
FIG. 5 shows an alternative composite image formed from the four corner images of FIG. 4.

FIG. 5 show an alternative composite image corresponding to the conventional 2D x-ray of a subject's torso 10 of FIG. 1, formed from just four non-adjacent corner regions 60. These corner regions would be sufficient to determine alignment of the emitters and detector.

Figure 6:
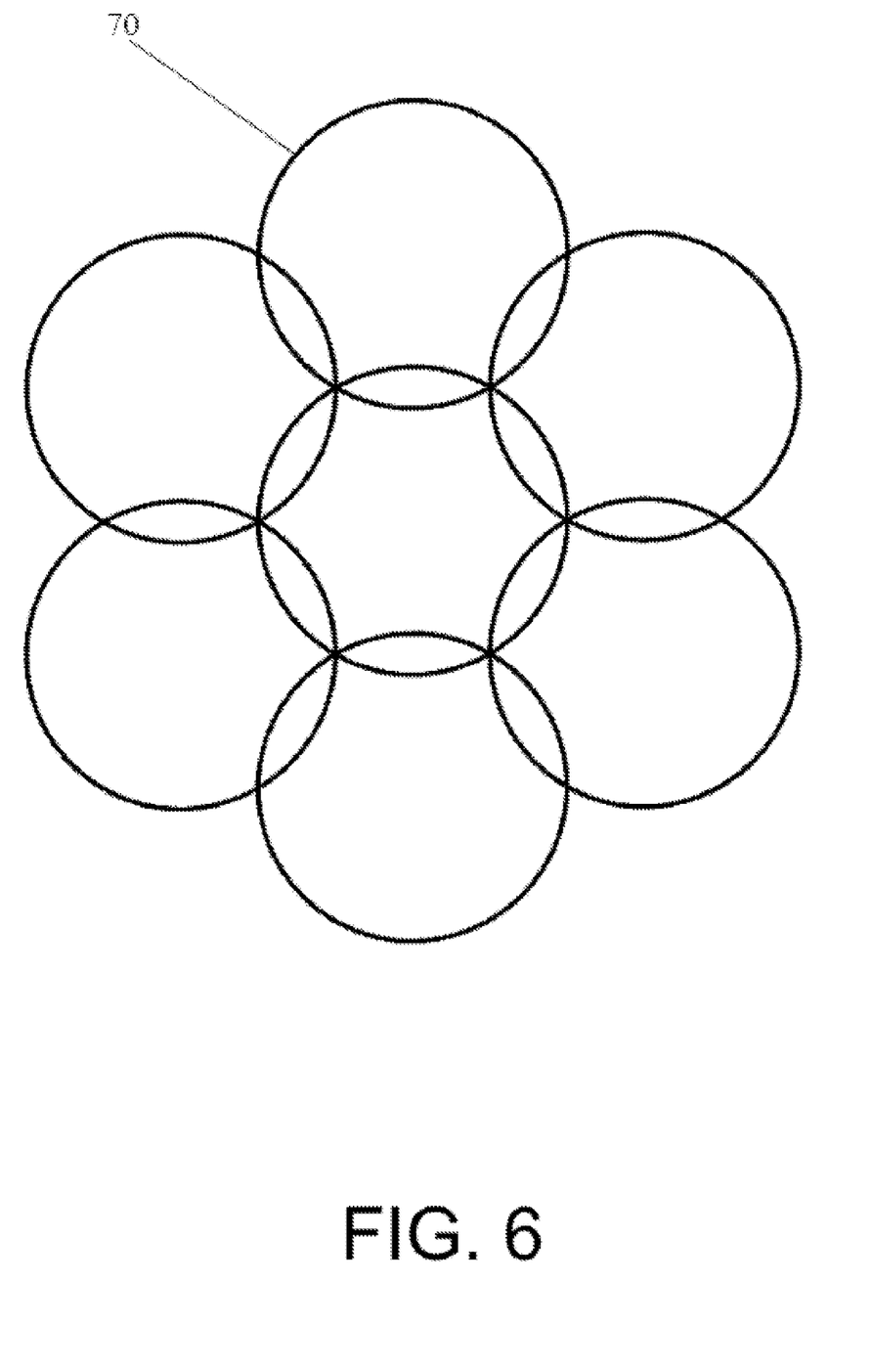
FIG. 6 shows an alternative arrangement of overlapping ellipse regions.

FIG. 6 shows an alternative arrangement of overlapping ellipse regions 70 arranged in a hexagonal pattern to ensure full coverage of the detector at minimum overlap.

Figure 7:
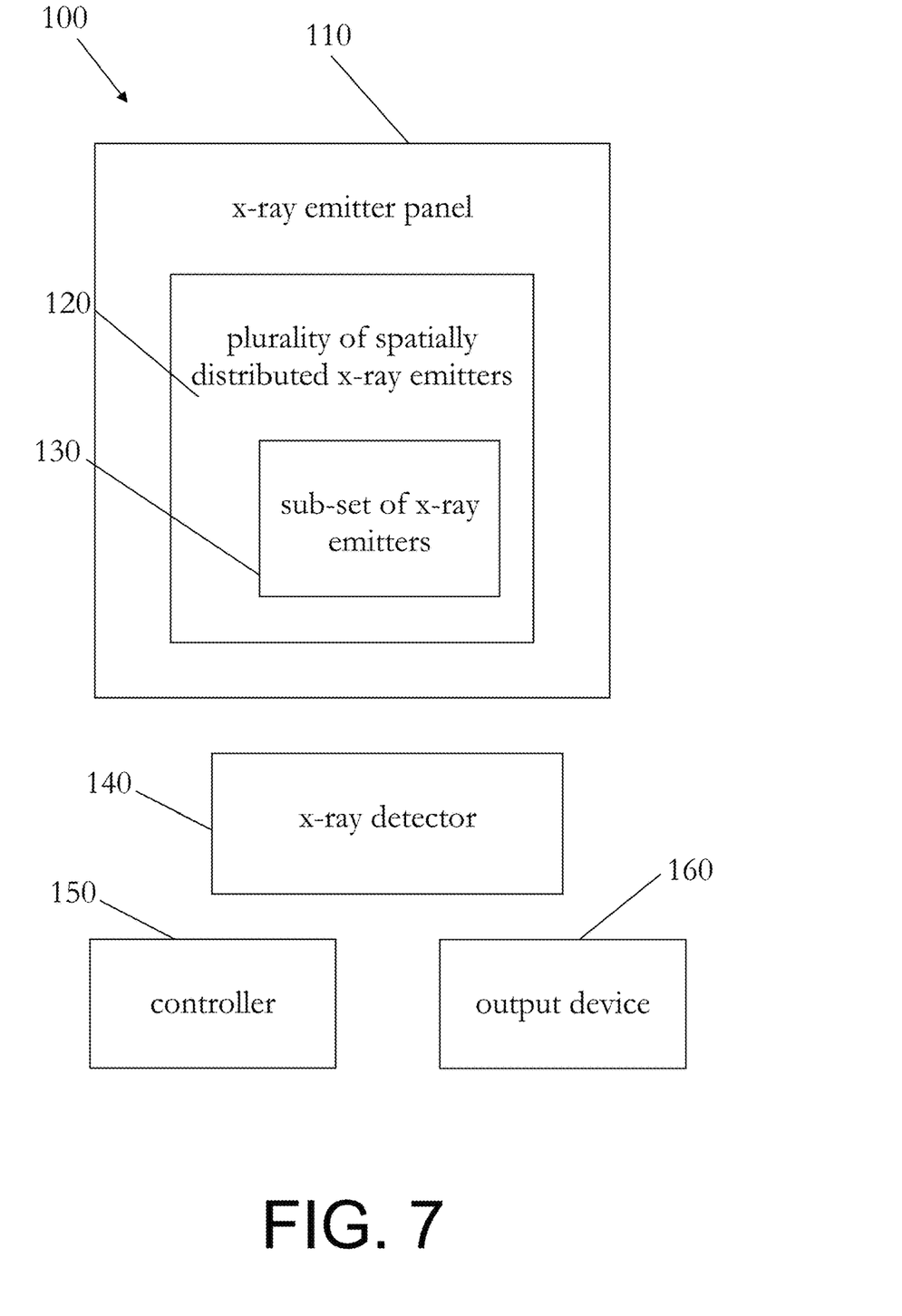
FIG. 7 shows a schematic diagram illustrating an digital x-ray tomosynthesis system.

FIG. 7 shows a schematic diagram illustrating an digital x-ray tomosynthesis system 100, comprising an x-ray emitter panel 110, an x-ray detector 140, a controller 150 and an output device 160. The x-ray emitter panel 110 comprises a plurality of spatially distributed x-ray emitters 120. The plurality of spatially distributed x-ray emitters 120 comprises a sub-set of x-ray emitters 130.

The invention claimed is:

1. A digital x-ray tomosynthesis system comprising:
   an x-ray emitter panel comprising a plurality of spatially distributed x-ray emitters arranged in a substantially planar array such that each respective emission cone from each respective one of the plurality of x-ray emitters projects along a respective axis substantially perpendicular to the planar array, when activated;
   an x-ray detector spaceable from the x-ray emitter panel by a separation distance such that each respective emission cone from each respective one of the plurality of x-ray emitters impinges on the x-ray detector, when activated;
   a controller configured to:
      select a sub-set of x-ray emitters from the plurality of x-ray emitters such that no part of the x-ray detector is exposed to x-rays from more than nine x-ray emitters of the sub-set of x-ray emitters;
      activate each x-ray emitter of the sub-set of x-ray emitters in a sequence to produce a respective image at the x-ray detector; and
      generate a two-dimensional composite image from non-overlapping portions of each of the respective images produced on the x-ray detector; and
   an output device configured to display the two-dimensional composite image generated by the controller to help with alignment of the system.

2. The system of claim 1, wherein the controller is configured to select the sub-set of x-ray emitters from the plurality of x-ray emitters such that each part of the x-ray detector is exposed to x-rays from at least one x-ray emitter of the sub-set of x-ray emitters, when activated.

3. The system of claim 1, wherein the controller is configured to select the sub-set of x-ray emitters from the plurality of x-ray emitters such that at least one part of the x-ray detector is not exposed to x-rays from any x-ray emitter of the sub-set of x-ray emitters, when activated.

4. The system of claim 1, wherein the controller is configured to select the sub-set of x-ray emitters from the plurality of x-ray emitters before activation of all x-ray emitters of the sub-set of x-ray emitters to produce the respective images at the x-ray detector.

5. The system of claim 4, wherein the controller is configured to activate each x-ray emitter of the plurality of x-ray emitters to produce a respective image at the x-ray detector and to reconstruct a 3D tomosynthesis image from the images at the x-ray detector produced by the plurality of x-ray emitters, in response to an input indicating acceptance of the composite image.

6. The system of claim 1, wherein the controller is configured to activate each x-ray emitter of the plurality of x-ray emitters to produce a respective image at the x-ray detector, and subsequently generate the composite image from non-overlapping portions of each of the respective images produced by the sub-set of the x-ray emitters.

7. The system of claim 6, wherein the controller is configured to reconstruct a 3D tomosynthesis image from the images at the x-ray detector produced by the plurality of x-ray emitters.

8. The system of claim 7, wherein the controller is configured to reconstruct the 3D tomosynthesis image at the same time as generating the composite image from the non-overlapping portions of each of the respective images produced by the sub-set of the x-ray emitters.

9. The system of claim 7, wherein the controller is configured to reconstruct the 3D tomosynthesis image after generating the composite image from the non-overlapping portions of each of the respective images produced by the sub-set of the x-ray emitters.

10. A method of presenting a 2D composite image to a user to help with alignment of an x-ray system, the method comprising the steps of:
   providing the system of claim 1;
   selecting a sub-set of x-ray emitters from the plurality of x-ray emitters such that no part of the x-ray detector is exposed to x-rays from more than nine x-ray emitters of the sub-set of x-ray emitters;
   activating each x-ray emitter of the sub-set of x-ray emitters to produce a respective image at the x-ray detector; and
   generating a two-dimensional composite image from non-overlapping portions of each of the respective images produced on the x-ray detector.

* * * * *